(12) United States Patent
Rundström et al.

(10) Patent No.: US 7,871,781 B2
(45) Date of Patent: Jan. 18, 2011

(54) TWO STEP LATERAL FLOW ASSAY METHODS AND DEVICES

(75) Inventors: Gerd Rundström, Uppsala (SE); Per Matsson, Knivsta (SE); Paul Christopher, Rhondda Cynon Taf (GB)

(73) Assignee: Phadia AB, Uppsala (SE)

( * ) Notice: Subject to any disclaimer, the term of this patent is extended or adjusted under 35 U.S.C. 154(b) by 195 days.

(21) Appl. No.: 11/438,882

(22) Filed: May 23, 2006

(65) Prior Publication Data

US 2007/0020768 A1 Jan. 25, 2007

Related U.S. Application Data

(60) Provisional application No. 60/683,702, filed on May 23, 2005.

(51) Int. Cl.
*G01N 33/53* (2006.01)
(52) U.S. Cl. .................... 435/7.1; 435/4; 435/5; 435/287.1; 435/287.7; 435/970; 435/975; 436/514; 436/518; 436/507; 436/530; 436/807; 436/821; 436/810; 422/56; 422/57; 422/58
(58) Field of Classification Search ............ 435/4, 435/5, 187.1, 287.7, 970, 975; 436/514, 436/518, 507, 530, 807, 821, 810; 422/56, 422/57, 58
See application file for complete search history.

(56) References Cited

U.S. PATENT DOCUMENTS

| | | | |
|---|---|---|---|
| 4,313,734 A | 2/1982 | Leuvering | |
| 4,376,110 A | 3/1983 | David et al. | |
| 4,477,575 A | 10/1984 | Vogel et al. | |
| 4,678,757 A | 7/1987 | Rapkin et al. | |
| 4,696,797 A | 9/1987 | Kelton | |
| 4,697,797 A | 10/1987 | Gold | |
| 4,703,017 A | 10/1987 | Campbell et al. | |
| 4,740,468 A | 4/1988 | Weng et al. | |
| 4,753,776 A | 6/1988 | Hillman et al. | |
| 4,775,636 A | 10/1988 | Moeremans et al. | |

(Continued)

FOREIGN PATENT DOCUMENTS

EP 253 464 1/1988

(Continued)

*Primary Examiner*—Bao-Thuy L Nguyen
(74) *Attorney, Agent, or Firm*—Porter, Wright, Morris & Arthur, LLP

(57) ABSTRACT

Lateral flow assay devices and methods for detecting an analyte in a sample which comprises a plurality of nonspecific binding pair members are adapted for two step determinations. In one embodiment, a method for identifying IgE antibodies in a sample comprises applying a sample to a sample port of a device, wherein the device is adapted to deliver the sample to a lateral flow matrix having a plurality of IgE antigen species immobilized at respective positions at a first location, allowing the sample to travel along the lateral flow matrix through the immobilized plurality of IgE antigen species to a second location downstream of the first location and allowing sample to dissolve a water-soluble mark, applying liquid buffer to the lateral flow matrix to mobilize labeled reagent which is adapted to bind anti-IgE antibody and which is dried on the lateral flow matrix at a location upstream of the sample delivery location, and allowing labeled reagent to bind any IgE antibody bound to the immobilized IgE antigen species therein.

46 Claims, 3 Drawing Sheets

U.S. PATENT DOCUMENTS

| | | | |
|---|---|---|---|
| 4,777,964 A * | 10/1988 | Briggs et al. | 600/573 |
| 4,788,152 A | 11/1988 | Doeding et al. | |
| 4,816,224 A | 3/1989 | Vogel et al. | |
| 4,818,677 A | 4/1989 | Hay-Kaufman et al. | |
| 4,855,240 A | 8/1989 | Rosenstein et al. | |
| 4,857,453 A | 8/1989 | Ullman et al. | |
| 4,861,711 A | 8/1989 | Friesen et al. | |
| 4,910,150 A | 3/1990 | Doeding et al. | |
| 4,916,056 A | 4/1990 | Brown et al. | |
| 4,933,092 A | 6/1990 | Aunet et al. | |
| 4,943,552 A | 7/1990 | Osajima et al. | |
| 4,956,302 A | 9/1990 | Gordon et al. | |
| 4,981,786 A | 1/1991 | Dafforn et al. | |
| 4,987,085 A | 1/1991 | Allen et al. | |
| 5,008,080 A | 4/1991 | Brown, III et al. | |
| 5,073,484 A | 12/1991 | Swanson et al. | |
| 5,091,318 A | 2/1992 | Anawis et al. | |
| 5,120,643 A | 6/1992 | Ching et al. | |
| 5,135,719 A | 8/1992 | Hillman et al. | |
| 5,137,808 A | 8/1992 | Ullman et al. | |
| 5,139,685 A | 8/1992 | de Castro et al. | |
| 5,149,622 A | 9/1992 | Brown et al. | |
| 5,160,701 A | 11/1992 | Brown, III et al. | |
| 5,260,221 A | 11/1993 | Ramel et al. | |
| 5,262,067 A | 11/1993 | Wilk et al. | |
| 5,308,775 A | 5/1994 | Donovan et al. | |
| 5,356,782 A | 10/1994 | Moorman et al. | |
| 5,364,533 A | 11/1994 | Ogura et al. | |
| 5,384,264 A | 1/1995 | Chen et al. | |
| 5,423,989 A | 6/1995 | Allen et al. | |
| 5,435,970 A | 7/1995 | Mamenta et al. | |
| 5,521,102 A | 5/1996 | Boehringer et al. | |
| 5,556,756 A | 9/1996 | Olsen et al. | |
| 5,558,834 A | 9/1996 | Chu et al. | |
| 5,559,041 A | 9/1996 | Kang et al. | |
| 5,591,645 A | 1/1997 | Rosenstein | |
| 5,602,040 A | 2/1997 | May et al. | |
| 5,622,871 A | 4/1997 | May et al. | |
| 5,650,333 A | 7/1997 | Holtlund et al. | |
| 5,654,162 A | 8/1997 | Guire et al. | |
| 5,656,503 A | 8/1997 | May et al. | |
| 5,691,207 A | 11/1997 | Holtlund et al. | |
| 5,712,172 A | 1/1998 | Huang et al. | |
| 5,714,389 A | 2/1998 | Charlton et al. | |
| 5,716,778 A | 2/1998 | Weng et al. | |
| 5,725,774 A | 3/1998 | Neyer | |
| 5,726,010 A | 3/1998 | Clark | |
| 5,726,013 A | 3/1998 | Clark | |
| 5,728,587 A | 3/1998 | Kang et al. | |
| 5,750,333 A | 5/1998 | Clark | |
| 5,766,961 A | 6/1998 | Pawlak et al. | |
| 5,770,460 A | 6/1998 | Pawlak et al. | |
| 5,798,215 A | 8/1998 | Cathey et al. | |
| 5,820,826 A | 10/1998 | Moorman | |
| 5,821,073 A | 10/1998 | Lee | |
| 5,879,881 A | 3/1999 | Rubenstein | |
| 5,916,521 A | 6/1999 | Bunce et al. | |
| 5,939,331 A | 8/1999 | Burd et al. | |
| 5,962,336 A | 10/1999 | Sun | |
| 5,989,921 A | 11/1999 | Charlton et al. | |
| 5,998,221 A | 12/1999 | Malick et al. | |
| 6,008,059 A * | 12/1999 | Schrier et al. | 436/518 |
| 6,046,058 A * | 4/2000 | Sun | 436/514 |
| 6,146,589 A | 11/2000 | Chandler | |
| 6,156,271 A | 12/2000 | May | |
| 6,187,598 B1 | 2/2001 | May et al. | |
| 6,197,598 B1 | 3/2001 | Schrier et al. | |
| 6,228,660 B1 | 5/2001 | May et al. | |
| 6,352,862 B1 | 3/2002 | Davis et al. | |
| 6,365,417 B1 | 4/2002 | Fleming | |
| 6,372,514 B1 | 4/2002 | Lee | |
| 6,485,982 B1 | 11/2002 | Charlton | |
| 6,528,325 B1 | 3/2003 | Hubscher et al. | |
| 6,534,320 B2 | 3/2003 | Ching et al. | |
| 6,541,277 B1 | 4/2003 | Kang et al. | |
| 6,689,317 B1 | 2/2004 | Rees | |
| 6,767,710 B2 | 7/2004 | DiNello et al. | |
| 6,818,455 B2 | 11/2004 | May et al. | |
| 6,824,975 B2 * | 11/2004 | Hubscher et al. | 435/4 |
| 7,189,522 B2 * | 3/2007 | Esfandiari | 435/7.1 |

FOREIGN PATENT DOCUMENTS

| | | | |
|---|---|---|---|
| WO | WO 99/36780 | * | 7/1999 |
| WO | 99/51988 A | | 10/1999 |
| WO | 00/07015 A | | 2/2000 |
| WO | 02/056017 A | | 7/2002 |
| WO | 03/048998 A | | 6/2003 |

* cited by examiner

TWO STEP LATERAL FLOW ASSAY METHODS AND DEVICES

RELATED APPLICATION

The present application claims priority under 35 U.S.C. §119 of U.S. application Ser. No. 60/683,702 filed May 23, 2005.

FIELD OF THE INVENTION

The present invention is directed to two step lateral flow assay methods and devices for detecting a first member of a specific binding pair in a sample. The methods and devices are particularly advantageous for detecting a first member of a specific binding pair in a sample which contains a plurality of nonspecific binding pair members. In specific embodiments, the methods and devices are advantageous for identifying specific IgE antibodies in a sample.

BACKGROUND OF THE INVENTION

Many lateral flow assay devices and methods are known in the art. Typically, the devices and methods allow for application of a sample to a lateral flow matrix. The sample flows along the lateral flow matrix, and one or more analyte components to be detected in the sample react with at least one reagent which is provided in or added to the lateral flow matrix. At least one reagent is typically immobilized in the device for reaction with the analyte component to be detected or a reagent thereof, and labels are typically employed to measure the extent of reaction with an immobilized reagent.

For example, the Dafforn et al U.S. Pat. No. 4,981,786 discloses an assay device for capturing a first member of a specific binding pair in a zone and for allowing liquid to be carried by capillary action away from the zone. A liquid reagent for conducting the assay, for example comprising a specific binding pair member, members of a signal producing system, ancillary reagents, or the like, is added. Dafforn et al disclose the specific use of their assay device and method for detecting the presence of human chorionic gonadotrophin (HCG).

To facilitate use of lateral flow assay devices by laboratory personnel and by non-laboratory medical personnel and consumers, for example in "point of care" applications, and to obtain quicker detection techniques, much attention has been directed to improving one-step assay devices and methods. For example, the May et al U.S. Pat. Nos. 5,602,040, 5,622,871, 5,656,503, 6,187,598 and 6,228,660 disclose devices, kits and methods which facilitate one-step lateral flow assay methods. A test strip is provided with a dried labeled reagent which is released into a mobile form by a liquid biological sample. The labeled reagent specifically binds with the analyte to be detected to form a complex, and the migration of the liquid sample along the lateral flow matrix conveys the complex by capillary action to a detection zone.

The Hubscher et al U.S. Pat. No. 6,528,325 discloses a more specific device and method for detection of antibodies in human serum by use of a lateral flow assay which facilitates one step techniques. A test sample obtained from bodily fluids reacts with a gold labeled antigen and the resulting complex travels across a membrane and along a lateral flow strip. Red colored lines formed in specific locations along the test strip indicate the presence of class specific antibodies in the test specimen. In a more specific embodiment disclosed by Hubscher et al, the lateral flow assay serves as an immunochromatographic screening test for the detection of allergen-specific IgE antibodies in human serum. Test sample reacts with gold labeled anti-IgE antibody and the resulting complex travels across the membrane where immobilized allergens capture the allergen specific IgE complex. Colored lines are formed in the test areas to indicate the presence of allergen-specific IgE antibodies.

Detection of specific allergies in an individual is important in allowing medical personnel to prescribe safe and effective allergy treatment. Common techniques for allergy detection typically involve skin prick testing to expose an individual to various allergens and/or complex and expensive laboratory testing. Because of the trauma, cost and/or inconvenience of commonly employed techniques, many medical personnel prescribe allergy treatments based only on an individual's symptoms, without testing to determine what specific allergies the individual may have. Such prescriptions obviously can be dangerous, wasteful and/or ineffective as individuals can be prescribed treatment medicines which are not proper for their allergy conditions. Accordingly, it would be advantageous to use lateral flow assay techniques for detection of IgE antibodies of an individual for accurate diagnosis of allergy in an individual. However, detection of specific IgE antibodies is often difficult. That is, biological samples such as blood contain a plurality of nonspecific binding members which interfere with reactions necessary for accurate labeling and detection of specific IgE antibodies.

More particularly, determination of a specific allergy requires identification of an IgE antibody having a variable region which binds to a specific allergen epitope. Bodily fluids typically contain thousands of antibodies of different IgE variable region specificities, and therefore, determination of a specific allergy by assay requires selective reaction of a single antibody type from the thousands of IgE antibody specificities. Detection conjugates readily bind to the constant regions of such IgE antibodies, i.e., the detection conjugates typically do not differentiate between different IgE specificities, and identification of a particular IgE antibody is difficult using conventional assay and label techniques. In practice, it has been difficult to conduct lateral assays using techniques as disclosed in the prior art to reliably identify IgE of an individual for diagnosing allergy. Typically, an immunoassay based on allergens bound on a solid phase, employing a detection conjugate binding to the non-variable region of IgE antibodies in the assay, will be sensitive to non-specific binding of IgE in the assay. Accordingly, a need exists for improved assay devices and methods, particularly for facilitating detection of specific IgE antibodies.

SUMMARY OF THE INVENTION

Accordingly, it is an object of the present invention to provide improved lateral flow assay devices and methods. It is a related object to provide lateral flow assay devices and methods which are advantageous for the detection of specific IgE antibodies and which therefore can assist in diagnosing allergy in an individual.

These and additional objects are provided by the present invention. In one embodiment, the invention is directed to a two step lateral flow assay method for identifying IgE antibodies in a sample. The method comprises applying a sample, for example whole blood or serum, to a sample port of a device which is adapted to deliver the sample to a lateral flow matrix having a plurality of IgE antigen species immobilized at respective positions at a first location. The device is optionally adapted to filter the sample to deliver a filtered sample, for example substantially free of red blood cells, to the flow matrix. The method further comprises allowing the sample to travel along the lateral flow matrix through the immobilized plurality of IgE antigen species to a second location downstream of the first location, applying liquid buffer to the lateral flow matrix to mobilize labeled reagent which is adapted to bind IgE antibody and which is dried on the lateral flow matrix at a location upstream of the delivery of the sample to the lateral flow matrix, and allowing labeled reagent mobilized by the liquid buffer to travel along the lateral flow matrix through the immobilized plurality of IgE antigen species to a location downstream of the first location.

The invention is further directed to a lateral flow immunoassay device for identifying IgE antibodies in a sample. The device comprises a housing provided with a sample port, a buffer port upstream of the sample port, a result window downstream of the sample port, and, optionally, a control window downstream of the result window. The device further comprises a buffer well upstream of the sample port and adapted to receive a quantity of liquid buffer applied through the buffer port, a lateral flow path within the housing, extending from the buffer well to a downstream location, for example the control window, if included, and comprising a lateral flow matrix, dried, labeled reagent adapted to bind IgE antibody, arranged on the lateral flow matrix downstream of the buffer well and upstream of the sample port, wherein the labeled reagent is adapted to be mobilized in the lateral flow matrix by liquid buffer passing from the buffer well along the lateral flow matrix, and a plurality of IgE antigen species immobilized at respective positions on the lateral flow matrix at a first location visible through the result window. The device may optionally further comprise unlabeled IgE or antimouse antibody immobilized on the lateral flow matrix at a second location separate and downstream from the first location and visible through the control window, if included in the housing.

In an alternate embodiment, the device comprises a housing provided with at least one sample port, at least one buffer port upstream of the sample port, at least one result window downstream of the sample port, and, optionally, at least one control window downstream of the result window, a buffer well upstream of the sample port and adapted to receive a quantity of liquid buffer applied through the buffer port, and at least two lateral flow paths within the housing, each extending from the buffer well to a downstream location, for example at least one of the control windows, if included, and comprising a lateral flow matrix. The device further comprises dried, labeled reagent adapted to bind with IgE antibody, arranged on each lateral flow matrix downstream of the buffer well and upstream of the sample port, wherein the labeled reagent is adapted to be mobilized in the lateral flow matrix by liquid buffer passing from the buffer well along the lateral flow matrix, and a plurality of IgE antigen species immobilized at respective positions on each lateral flow matrix at a first location visible through at least one of the result windows. The device may optionally include unlabeled IgE or anti mouse antibody, immobilized on each lateral flow matrix at a second location separate and downstream from the first location and visible through at least one of the control windows, if included in the housing.

In yet further embodiments, the present invention is directed to lateral flow assay devices and methods for detecting a first member of a specific binding pair in a sample which comprises a plurality of nonspecific binding pair members. The device comprises a housing provided with one sample port, one buffer port upstream of the sample port, at least one result window downstream of the sample port, and optionally at least one control window downstream of the result window, a buffer well upstream of the sample port and adapted to receive a quantity of liquid buffer applied through the buffer port, and at least two lateral flow paths within the housing, each extending from the buffer well to a downstream location, for example at least one of the control windows, and comprising a lateral flow matrix. The device further comprises a dried, labeled reagent capable of binding with the first member of the specific binding pair, the labeled reagent being arranged on each lateral flow matrix downstream of the buffer well and upstream of the sample port, wherein the labeled reagent is adapted to be mobilized in the lateral flow matrix by liquid buffer passing from the buffer well along the lateral flow matrix, and a second member of the specific binding pair immobilized on each lateral flow matrix at a first location visible through at least one of the result windows. The device may optionally include a quantity of the first member of the specific binding pair, unlabeled and immobilized on each lateral flow matrix at a second location separate and downstream from the first location and visible through at least one of the control windows.

In another embodiment, a two step lateral flow assay method according to the invention for detecting a first member of a specific binding pair in a sample which comprises a plurality of nonspecific binding pair members comprises applying the sample to a lateral flow matrix having a second member of the specific binding pair immobilized at a first location, allowing the sample to travel along the lateral flow matrix through the immobilized second member of the specific binding pair to a second location downstream of the first location, applying liquid buffer to the lateral flow matrix to mobilize labeled reagent dried on the lateral flow matrix at a location upstream of the delivery of the sample to the lateral flow matrix, the labeled reagent being capable of binding with the first member of the specific binding pair, and allowing labeled reagent mobilized by the liquid buffer to travel along the lateral flow matrix through the immobilized second member of the specific binding pair to a location downstream of the first location. The invention is also directed to a lateral flow assay device for conducting such a method.

The devices and methods of the present invention are advantageous in many respects. For example, as the sample is contacted with the immobilized reagent prior to its contact with labeled reagent, the labeled reagent does not interfere with reactions between sample analyte and immobilized reagent. Surprisingly, this has been found to be particularly important when the sample analyte comprises a plurality of nonspecific binding pair members, for example when the sample comprises IgE antibodies and detection of individual IgE antibody types is desired. Unexpectedly, the present methods and devices provide significantly improved IgE detection. Additionally, the devices and methods allow convenient and efficient detection of a plurality of analytes in a sample using a single device, and the devices and methods of the invention may be easily and accurately used by medical personnel to allow point of care testing.

These and additional objects and advantages will be more fully apparent in view of the following detailed description.

BRIEF DESCRIPTION OF THE DRAWING

The following detailed description will be more fully understood in view of the drawing in which.

Figure 1:
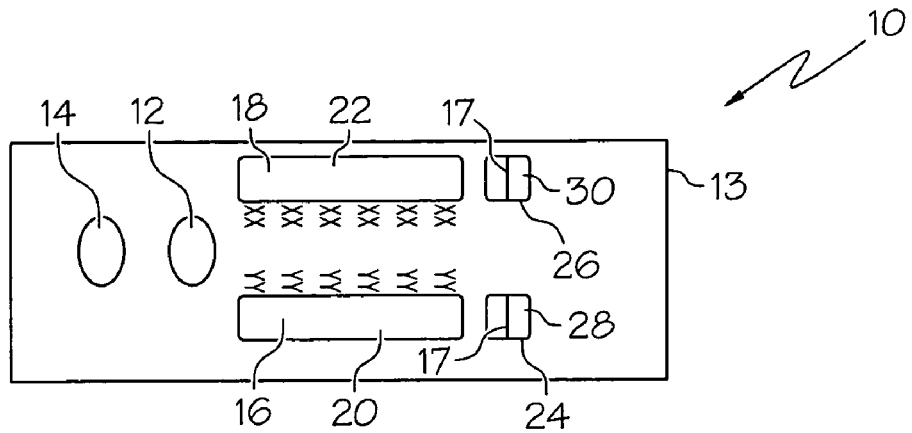
FIG. 1 is a schematic top view of a housing in one embodiment of a device according to the present invention containing two lateral flow matrices.

The embodiments set forth in the drawing are illustrative in nature and are not intended to be limiting of the invention defined by the claims. Moreover, individual features of the drawing and the invention will be more fully apparent and understood in view of the detailed description.

DETAILED DESCRIPTION

The present invention is directed to two step lateral flow assay devices and methods. The methods and devices are particularly suitable for conducting immunoassays to determine, qualitatively or quantitatively, if a sample contains a first member of a specific binding pair. While specific devices and methods described herein are indicated as useful and advantageous for identifying IgE antibodies in a sample, for example whole blood, or a blood component it is equally within the scope of the inventive devices and methods to be used for detecting other analytes in various biological fluid samples, including plasma, serum, urine, saliva or the like. Examples of other analytes which may be detected according to the present devices and methods include, but are not limited to, various proteins, including, but not limited to, proteins having particular biological functions such as antibodies and other proteins found in human plasma, proteins related to specific microorganisms, particularly disease-causing microorganisms, protein hormones, and the like.

In one embodiment, the device of the present invention comprises a housing provided with a sample port, a buffer port upstream of the sample port, a result window downstream of the sample port, and, optionally, a control window downstream of the result window, a buffer well upstream of the sample port and adapted to receive a quantity of liquid buffer applied through the buffer port, and a lateral flow path within the housing, extending from the buffer well to a downstream location, for example, the control window, and comprising a lateral flow matrix. The device further comprises a dried, labeled reagent, for example, labeled anti-IgE antibody, capable of binding with the first member of the specific binding pair, for example IgE antibodies, the labeled reagent being arranged on the lateral flow matrix downstream of the buffer well and upstream of the sample port, wherein the labeled reagent is adapted to be mobilized in the lateral flow matrix by liquid buffer passing from the buffer well along the lateral flow matrix, and a second member of the specific binding pair, for example, a plurality of IgE antigens, immobilized on the lateral flow matrix at a first location visible through the result window. The device may optionally include a quantity of unlabeled reagent capable of binding with the labeled reagent, conveniently unlabeled first member of the specific binding pair, for example, unlabeled IgE antibody, immobilized on the lateral flow matrix at a second location separate and downstream from the first location and visible through the control window, if included.

In a specific embodiment, the device comprises a plurality of IgE antigen species immobilized at respective positions on the lateral flow matrix at the first location, and provides point of care testing for the detection of IgE antibodies against a range of potential IgE allergens from a blood sample. The blood sample may comprise whole blood, or a separated blood component, for example serum or plasma.

FIG. 1 shows a schematic top view of a housing of a device 10 according to one embodiment of the invention. The housing may be formed of any suitable material, an example of which comprises molded plastic, and is preferably sufficiently rigid to provide support and stability for the lateral flow path or paths housed therein. A single oval-shaped sample port 12 is provided in the housing top 13, together with a single oval-shaped buffer port 14 upstream of the sample port 12. Although additional sample and/or buffer ports may be provided, it is preferred that the housing include only one of each in order to facilitate easy and convenient use of the device. In the embodiment of FIG. 1, two result windows 16 and 18 are provided in the housing top 13 downstream of the sample port 12 and over respective detection zones 20 and 22 in respective lateral flow paths, and two control windows 24 and 26 are provided in the housing top 13 downstream of the result windows 16 and 18 and over respective control zones 28 and 30 in respective lateral flow paths. The result windows 16 and 18 and the control windows 24 and 26 may be composed of merely openings in the housing top, or, alternatively, a transparent covering may be provided in one or more of the openings. While the device shown in FIG. 1 comprises two result windows and two control windows, it should be understood that a single result window and/or a single control window may be employed, or, alternatively, additional result windows and/or control windows may be provided as desired. In the embodiment of FIG. 1, a lateral flow path is associated with one result window and one control window, although such a one to one correspondence is not required. It is equally within the scope of the present invention to omit the control windows 24 and 26 from the housing and to omit the control zones 28 and 30 from the respective lateral flow paths, if not is not desired to provide a visual control signal in the device.

Figure 2:
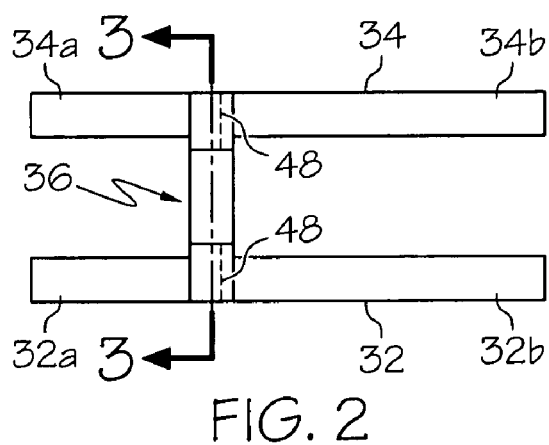
FIG. 2 is a schematic top view of a lateral flow matrix of a device according to FIG. 1 in combination with a blood separation system in another embodiment according to the present invention.
Figure 3:
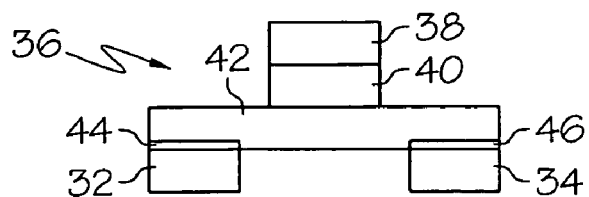
FIG. 3 is a cross sectional view taken along line 3-3 in FIG. 2.

The housing top 13 as described fits together with a housing bottom to enclose two lateral flow paths therein. As set forth above, the device may alternatively comprise one flow path, or three or more lateral flow paths, as desired. FIG. 2 sets forth a top view of the two lateral flow paths contained within the housing of the device, in combination a blood separation system. FIG. 3 is taken along line 3-3 of FIG. 2 and shows the combination in further detail. With reference to FIGS. 2 and 3, parallel lateral flow paths 32 and 34 include upstream portions 32a and 34a which are upstream of blood separation system 36 and downstream portions 32b and 34b which are downstream of the blood separation system 36.

The blood separation system 36 is adapted to underlie the sample port 12 in the housing top and to extend between the sample port and the lateral flow paths. The blood separation system may include at least one layer of material adapted to aggregate red blood cells therein so that the sample that passes to the lateral flow paths will be substantially free of red blood cells. The blood separation system 36 comprises a top glass fiber filter paper layer 38, a middle glass fiber filter paper layer 40, and a bottom glass fiber filter paper layer 42. At least one of, and preferable both of, the top and middle filter paper layers 38 and 40 contain an aggregating agent therein. Numerous aggregating agents are known in the art and are suitable for use herein. For example, the aggregating agent may comprise, but is not limited to, a sugar such as mannitol, sorbitol or inositol, one or more red blood cell-binding antibodies, lectins, or the like. In the assembled lateral flow assay device, the layers 38 and 40 are arranged under the sample port 12 and are large enough to receive a sample from the sample port, but do not extend laterally to the lateral flow paths 32 and 34. The bottom layer 42 is arranged below layer 40 and extends laterally to contact each of two lateral flow strips. The bottom filter paper layer 42 may also comprise a red blood cell aggregating agent if desired. This layer may also contain one or more additives to facilitate flow of the filtered sample received from layers 38 and 40 to the lateral flow paths 32 and 34. For example, in one embodiment, the layer 42 comprises polyvinyl alcohol bound to the glass fibers. To facilitate flow along the lateral flow matrix in the downstream direction, contact between the bottom layer 42 and the lateral flow paths is limited at the upstream side by arrangement of thin, liquid impervious layers 44 and 46 between the layer 42 and the lateral flow paths 32 and 34, respectively. For example, layers 44 and 46 may be formed of a lamination tape or the like. The downstream edge of each of the layers 44 and 46 is shown by a phantom line 48 in FIG. 2, illustrating the area downstream of the edges 48 where the layer 42 contacts the lateral flow paths 32 and 34.

The blood separation system 36 may be included in the inventive device when it is desirable to use a sample which is desirably filtered to remove components which may interfere with a visual signal, i.e., a whole blood sample wherein red blood cells are desirably removed. On the other hand, the blood separation system may be omitted if the intended sample does not require filtering of any components therefrom, i.e., a serum sample. Alternatively other blood or sample separation systems may be included in the inventive devices as desired.

Figure 4:
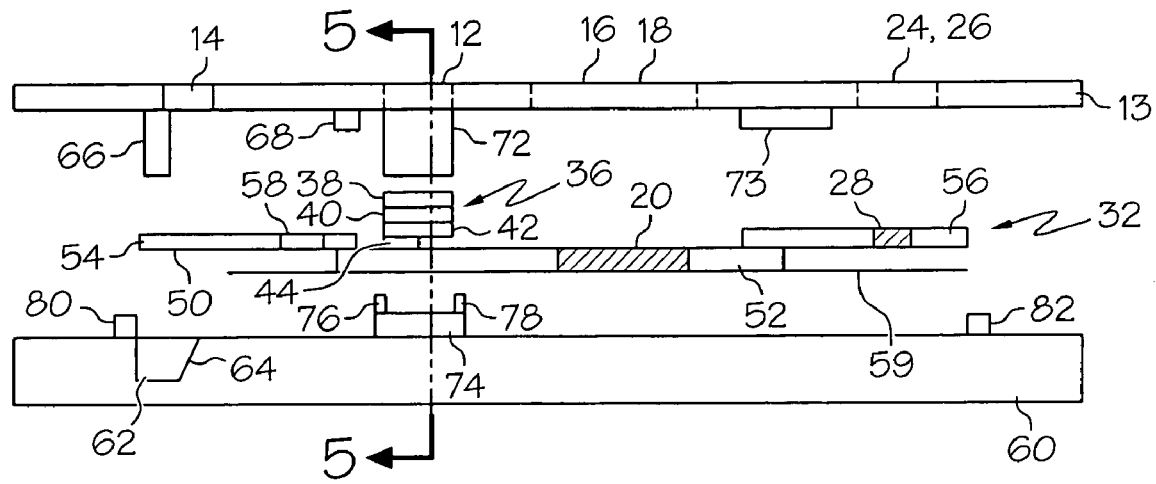
FIG. 4 is a schematic exploded side view of a device according to the present invention.
Figure 5:
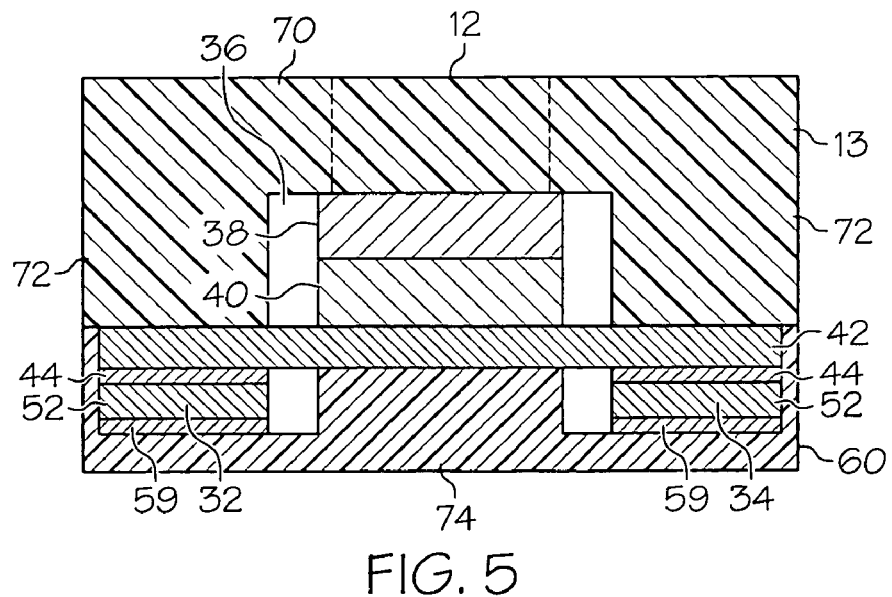
FIG. 5 is a cross sectional view taken along line 5-5 of FIG. 4, of the device according to the present invention in assembled form.

FIG. 4 shows an expanded side view of a device according to the invention, while FIG. 5 shows a cross-sectional view of the device taken along line 5-5 once the device has been assembled within the device housing. With reference to FIG. 4, lateral flow path 32 is described. However, lateral flow path 34 includes similar features as described with respect to lateral flow path 32 although the lateral flow path 34 is not shown in the side view of FIG. 4. Each lateral flow path of the device of the illustrated embodiment includes a lateral flow matrix 50 which is porous or bibulous and promotes lateral flow of liquids applied thereto by capillary action. The lateral flow matrix 50 shown in FIG. 4 comprises a main strip 52 which extends from a position upstream of the sample port 12 and the blood separation system 36 to a position downstream of the corresponding result window 16, 18. The main strip 52 may be formed of any desirable flow material, including, but not limited to, cellulosic materials and materials derived from cellulose, such as filter paper, nitrocellulose, and cellulose acetate, or a polymer, including, but not limited to nylon, silicone, or the like. The pores of the material must be sufficiently large to allow flow therethrough of the sample and labeled reagent described in further detail below. Suitable pore sizes are typically in the range of from about 0.4 to about 1000 microns, with pore sizes in the range of from about 0.4 to about 100 being suitable in many instances. In a specific embodiment, the main strips 52 are formed of nitrocellulose. Each main strip 52 is in fluid flow communication with the blood separation system 36 via a portion of the bottom glass fiber filter layer 42, although contact therebetween is limited by, for example, a lamination tape layer 44.

Each main strip 52 of the lateral flow paths 32 and 34 includes, at a first location, respective detection zones 20 and 22 which are visible through the corresponding result windows 16 and 18. Each detection zone has immobilized thereon at least one second member of the specific binding pair for reaction with and immobilization of the first member contained in the sample. In a specific embodiment as disclosed herein, the detection zone of each main strip contains a series of IgE allergens specific for a series of IgE antibodies desired for detection. The antigens are applied such that each type of antigen is immobilized at a separate location within the detection zone. Various combinations of IgE antigens may be employed as desired. For example, IgE antigens suitable for immobilization within the detection zones include, but are not limited to, pollens, for example, Timothy, cultivated rye, birch, alder, hazelnut, mugwort, English plantain, ragweed, and/or nettle, dust allergens, for example, *D. farinae, D. pteronyssinus*, and/or house dust, molds, for example, *Alternaria tenuis, Aspergillus fum., Cladosporium*, and/or *Penicillium not*, animal epithelium, for example, cat dander, dog dander, horse dander, and/or goose feathers, foods, for example, dairy, cereals, nuts, seafoods, and/or legumes, inhalant mixes, for example, pollen I (grasses), pollen II (weed/tree), animal mix, dust mix, and/or mold mix, and the like. The IgE allergens, or other second specific binding pair member(s), are attached to the main test strip at the detection zone in any manner known in the art which is sufficient to immobilize the member(s) in the flow matrix and to maintain the immobilization under the assay conditions.

In one embodiment, the IgE allergens are immobilized in the flow matrix by attaching the respective allergens to particles which are, in turn, immobilized in the pores of the flow matrix. Such immobilizing particles are known in the art and include, for example, silicon dioxide particles and organic polymer particles such as synthetic addition polymers, synthetic condensation polymers and biopolymers, optionally synthetically cross linked. The particles are suitably of a size which can be received and maintained within the pores of the flow matrix. In one embodiment, the immobilizing particles have a diameter smaller than a smallest inner dimension of flow channels of the lateral flow matrices in the first location of the detection zones. Examples of suitable particles include those as taught in the published Pharmacia Diagnostics AB PCT application WO 99/36780, which is incorporated herein by reference. In one embodiment, the immobilizing particles are formed of synthetic polymer latex, for example, polystyrene homopolymer or copolymer latex particles, and have been treated with hydrophilic groups such as alcoholic hydroxyl groups to improve the immobilization and reaction of the antigens or other second specific binding pair member, as also taught in the aforementioned published Pharmacia Diagnostics AB PCT application WO 99/36780.

As shown in FIG. 1, the outer surface of the housing top 13 may be provided with indicia 15 adjacent each result window in order to distinguish the locations of the respective species of IgE antigens which are immobilized in the respective detection zones. The indicia may comprise text, graphics, icons, or any combinations thereof. These indicia may then assist medical personnel in reading any positive results which are presented once the device has been employed to conduct an assay.

Each lateral flow matrix 50 further includes an upstream lower wick 54 which is in fluid flow communication with the upstream end of the main strip 52, and a downstream upper wick 56 which is in fluid flow communication with the downstream end of the main strip 52. When the housing is provided with control window(s), the upper wick may be arranged under the respective control window. Thus, as shown in FIG. 4, each upper wick 56 is arranged under the respective control window 24, 26. The upper and lower wicks 54 and 56 are formed of any desirable flow material, including, but not limited to, cellulosic materials and materials derived from cellulose, such as filter paper, nitrocellulose, and cellulose acetate, nylon and the like. In a one embodiment, the wicks are formed of glass fiber filter paper.

At a location upstream of its contact point with the main strip 52, each lower wick 54 includes a dried labeled reagent 58. The labeled reagent is adapted to be mobilized for flow through the lateral flow matrix once a liquid buffer is applied to the device as will be described in further detail below. The labeled reagent must be able to react with the first member of the specific binding pair at a binding site different from that with which the first specific binding pair member reacts with the immobilized second specific binding pair member. Additionally, the labeled reagent either includes a visibly detectable label or is reactive with a visibly detectable label. In a specific embodiment, the labeled reagent includes a visibly detectable label. Such labels are well known in the art and include, but are not limited to, chromophores, fluorophores, radioactive compounds, enzymes and the like, and any such label may be employed on the labeled reagent. The labeled reagent may comprise particles to facilitate its use in accordance with techniques known in the art, including, but not limited to metal sol particles. In one embodiment, the labeled reagent is adapted to bind with IgE antibody. In a more specific embodiment, the labeled reagent comprises labeled anti-IgE antibody. In a more specific embodiment, the labeled reagent comprises gold sol-labeled anti-IgE antibody and is provided, for example, on the lower wick by spraying a solution of gol sol particles having anti-IgE antibody thereon onto the glass fiber filter paper and allowing the sprayed solution to dry.

Each upper wick 56 may optionally include a control zone 28, 30 under the respective control window 24, 26. Each control zone is provided with a dried control reagent comprising a quantity of unlabeled reagent capable of binding with the labeled reagent. In one embodiment, the unlabeled reagent comprises the first member of the specific binding pair. The dried control reagent is immobilized in the lateral flow path at a second location in the control zone which is downstream from the first location in the detection zone and which is visible through at least one control window. This immobilized first member is unlabeled and, as will be discussed below, may be used to confirm that the assay device has operated properly. For example, in one embodiment, each control zone comprises unlabeled, immobilized IgE or anti mouse antibody.

In a further embodiment, each control zone is initially provided with at least one visible marking of water soluble dye which is visible through a control window. The visible marking of water soluble dye may be in any form, for example a line 17 as shown in FIG. 1. As will be described below, this marking may be used to confirm that a sample has been properly applied to the assay device during use and as a signal to complete the assay procedure by application of liquid buffer. In one embodiment, the water soluble dye marking is of a color which is different from any visible color of the labeled reagent label, and/or the water soluble dye marking is of a shape which is different from the shape or pattern of the control reagent applied in the control zone. As a result, a user will be able to easily distinguish between the water soluble dye marking and any marking which subsequently appears in the control zone as a result of labeled reagent binding therein.

The downstream end of the upper wicks 56 may optionally be in contact with a sink for collecting excess liquid from the lateral flow matrices. Such a sink may further assist in promoting lateral flow along each matrix.

As shown in FIGS. 4 and 5, the device further includes a bottom housing 60 which is provided with a buffer well 62. The buffer well 62 is arranged under the buffer port 14 for receiving a liquid buffer applied to the device through the buffer port 14. The buffer port is of a size which is sufficiently large to hold a quantity of buffer liquid, i.e. saline, which is effective to mobilize the dried labeled reagent on each lower wick 54 and transport the mobilized labeled reagent along each lateral flow matrix to the respective control zone 28, 30 on the respective upper wick 56. The buffer well extends laterally across the device so that the upstream end of each lower wick 54 of each lateral flow path will be in fluid flow contact with the liquid buffer in the well once the buffer is applied to the device. Thus, a single application of the buffer liquid will activate lateral flow in each lateral flow path. To facilitate lateral flow of the buffer liquid from the buffer well 62 and along each lower wick 54, the downstream wall of the buffer well may be sloped as shown at 64.

Additionally, a liquid impervious layer or support may be provided to underlie the lateral flow matrix. As shown in FIG. 4, a liquid impervious layer 59 is provided under the portion of the lower wick 54 extending from the buffer well 62, the main strip 52, and the upper wick 56. In a specific embodiment, the layer is formed of an adhesive coated plastic film which is assembled with the adhesive facing the lateral flow matrix to assist in maintaining the lateral flow matrix in position on the lateral flow path.

FIGS. 4 and 5 also show that the housing may include one or more pressure bars, supports and/or locating pegs for arranging the various layers and strips in the housing and maintaining them in position in the assembled device. For example, the housing top 13 is provided with a pressure bar 66 for maintaining the upstream portion of the lower wicks 54 in place at the buffer well and a pressure bar 68 for maintaining the downstream ends of the lower wicks 54 and the upstream ends of the main strips 52 in contact with one another and in place in the assembled device. In the area of the blood separation system 36, the housing top 13 is provided with a pressure bar 70 for maintaining the layers 38 and 40 in position below the sample port 12 and with pressure bars 72 on each side of the pressure bar 70 for maintaining the layer 42 and thin layers 44 in contact with the main strips 52 of the lateral flow paths 32 and 34. Further, the housing top includes a pressure bar 73 for maintaining the downstream ends of the main strips 52 and the upstream ends of the upper wicks 56 in contact with one another and in place in the assembled device. In one embodiment, these pressure bars may be formed integrally with the housing top 13, for example when the housing top is formed of molded plastic. Alternatively, one or more of the pressure bars may be provided as separate components. In a specific embodiment, the housing top is free of any pressure bars in the area of the result windows to prevent any pressure application in the area of the detection zones.

The housing bottom 60 may be provided with one or more supporting or locating structures. In the embodiment shown, the housing bottom 60 includes a support bed 74 which assists in maintaining the blood separation system 36 in position under the sample port 12 and aligned with the main strips 52. In the region adjacent layers 38 and 40, the support bed 74 includes upstream and downstream flanges 76 and 78 to facilitate sample flow to the underlying layer 42 and the main strips 52 and/or to further assist in maintaining the blood separation system in position. Further, the housing bottom 60 includes an upstream locating peg 80 to assist location of the upstream end of the lower wicks 54 at the buffer well, and downstream peg 82 to assist location of the downstream end of the upper wicks 56 in the region of the control zones. Each wick and/or strip optionally may be provided with one or more notches, perforations or holes for receiving a locating peg or a portion of a locating peg to further assist in maintaining the strip in position.

Figure 6:
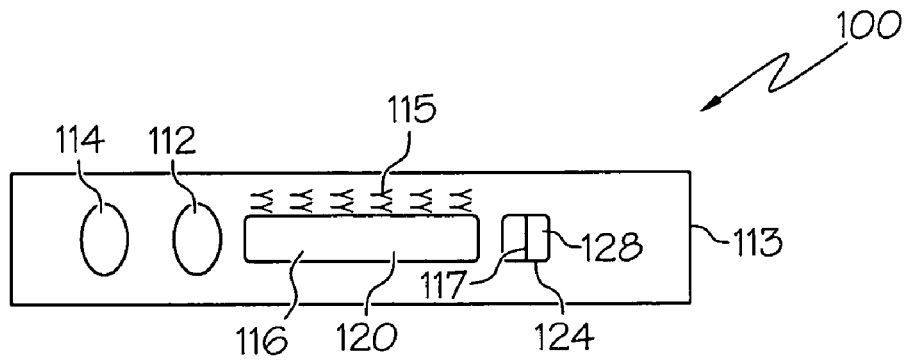
FIG. 6 is a schematic top view of a housing in another embodiment of a device according to the invention containing one lateral flow matrix.
Figure 7:
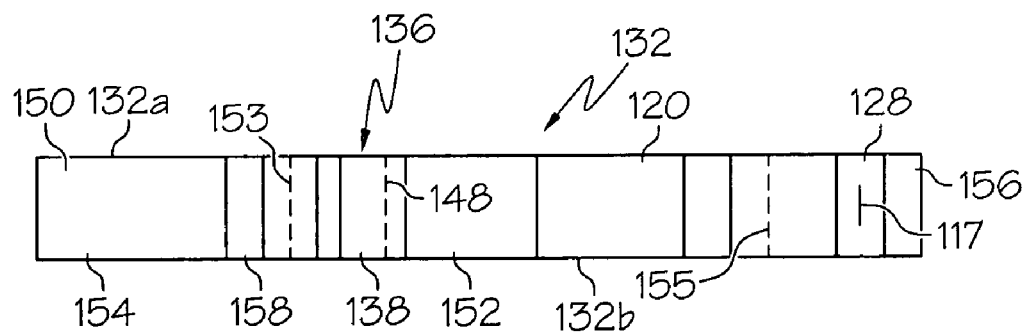
FIG. 7 is a schematic top view of a lateral flow matrix of the device of FIG. 6 according to the invention containing one lateral flow matrix.
Figure 8:
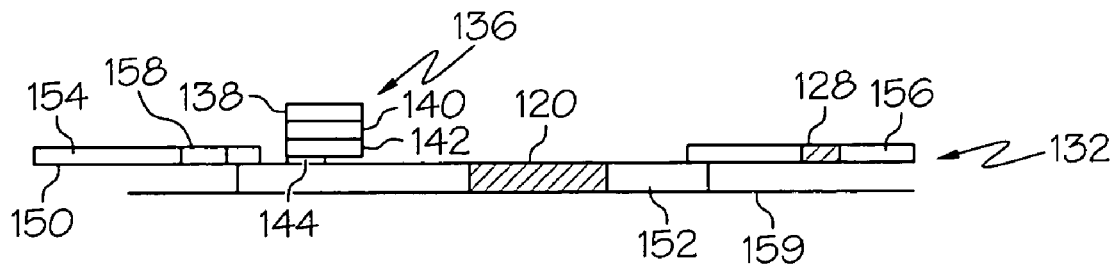
FIG. 8 is a schematic side view of the lateral flow matrix of the device of FIG. 7.

FIGS. 6-8 are directed to another embodiment of a device according to the present invention, which device contains a single lateral flow matrix. More particularly, the housing is similar in construction to that described in further detail in connection with FIG. 1, and includes a housing top 113 which is provided with a single oval-shaped sample port 112 and a single oval-shaped buffer port 114 upstream of the sample port 112. Additional sample and/or buffer ports may be provided, although it is preferred that the housing only include one of each in order to facilitate easy and convenient use of the device. The housing top 113 is further provided with a result window 116 downstream of the sample port 112 and arranged over a detection zone 120 contained in the lateral flow path. The housing 113 may be further provided with a control window 124 downstream of the result window 116 and over a control zone 128. As previously described, the control zone 128 is optionally included in the device, and, in turn may optionally be provided with at least one visible marking, for example, of water soluble dye, indicated in FIG. 6 at 117, which is visible through the control window. The marking 117 may be used to confirm that a sample has been properly applied to the assay device during use and as a signal to complete the assay procedure by application of liquid buffer. The result window 116 and the control window 124 may be composed of merely openings in the housing top, or, alternatively, a transparent covering can be provided in one or both of the openings. The housing top 113 may also be provided with indicia 115 adjacent the result window in order to distinguish the locations of respective specific binding pair members immobilized in the detection zone, for example to distinguish the locations of respective species of IgE antigens which are immobilized in the detection zone 120.

FIG. 7 shows a schematic top view of a lateral flow matrix suitable for use in the device of FIG. 6, while FIG. 8 shows a schematic side view of the lateral flow matrix of FIG. 7. With reference to FIG. 7, the lateral flow path 132 includes an upstream portion 132a which is upstream of a blood separation system 136 and a downstream portion 132b which is downstream of the blood separation system 136. As in the previously discussed embodiment, the blood separation system 136 is adapted to underlie the sample port 112 in the housing top. The blood separation system may include any of the embodiments previously discussed with respect to the blood separation system 36, or may be omitted, if desired. In the embodiment shown in FIG. 8, the system 136 comprises a top glass fiber filter paper layer 138, a middle glass fiber filter paper layer 140, and a bottom glass fiber filter paper layer 142. One or more of the glass fiber filter paper layers may include aggregating agent to remove red blood cells from the samples and/or additives to facilitate flow of a filtered sample to the lateral flow path 132. To facilitate flow along the lateral flow matrix in the downstream direction, contact between the bottom layer 142 and the lateral flow path is limited at the upstream side of the layer 142 by arrangement of a thin liquid impervious layer 144 between the upstream portion of the layer 142 and the lateral flow path 132. The layer 144 may be formed of a lamination tape or the like, and the downstream edge of the layer 144 is shown by a phantom line 148 in FIG. 7.

The lateral flow path includes a lateral flow matrix 150 which is porous or bibulous and promotes lateral flow of liquid applied thereto by capillary action. As shown in FIG. 8, the lateral flow matrix includes a main strip 152 which extends from a position upstream of the sample port 112 and the blood separation system 136 to a position downstream of the result window 116. The main strip 152 may be formed of any desirable flow material, including those described previously with respect to the main strip 52. The main strip 152 includes the detection zone 120 having immobilized thereon at least one second member of the specific binding pair for reaction with an immobilization of the first member contained in a sample. In a specific embodiment, the detection zone of the main strip 152 contains a plurality of IgE allergens specific for a series of IgE antibodies desired for detection.

The lateral flow matrix 150 further includes an upstream lower wick 154 which is in fluid flow communication with the upstream end of the main strip 152, and a downstream upper wick 156 which is in fluid flow communication with the downstream end of the main strip 152. In FIG. 7, the upstream edge of the main flow strip 152 is shown by phantom line 153, while the downstream edge of main stream 152 is shown by phantom line 155. At a location upstream of its contact point with the main strip 152, the upstream lower wick 154 includes dried labeled reagent 158, which is adapted to be mobilized for flow through the lateral flow matrix once a liquid buffer is applied to the device in a manner as previously described. Thus, the upstream end of upper wick 154 preferably extends into a buffer well contained in the bottom housing of the device in a manner as shown in FIG. 4. The downstream upper wick 156 is arranged under the control window 124 with the immobilized unlabeled reagent 128 at a position appearing through the control window 124 as shown in FIG. 6.

The lateral flow matrix may be arranged and maintained in the device housing in any manner known in the art, including those discussed above with respect to FIGS. 4 and 5. In one embodiment, a liquid impervious layer or support 159 is provided to underlie the lateral matrix.

In operation of the devices according to the invention, a sample is collected. For example, when identification of IgE antibodies is desired, a whole blood sample is collected, although a separated blood component, or other sample, may be employed. Sample collection is preferably conducted in a capillary device of a size sufficient to provide a sample volume appropriate for travel along the lateral flow matrix to the control zone of the lateral flow path(s) within the device. Application of a measured quantity of sample, as from a capillary, will assist in preventing application of a quantity of sample in excess of that needed for the proper use of the device. The capillary may optionally contain an anti-coagulant, for example, heparin. The whole blood sample is supplied to the sample port from the capillary device. As the blood sample travels downwardly from the sample port through the top, middle and bottom glass fiber filter paper layers, red blood cells are aggregated and retained in the filter paper layers. That is, the aggregating agent such as mannitol which is contained in the top and middle filter paper layers acts as an agglomerating agent for the red blood cells to prevent them from passing through the filter paper layers. As a result, a red blood cell-free plasma sample is delivered from the bottom glass fiber filter paper layer to the main strip of the lateral flow path(s).

Once the plasma sample contacts the main strip(s), the sample flows laterally towards the respective detection zone under the result window where specific IgE antibody analyte in the sample will bind to the respective immobilized specific IgE allergen particles. The sample plasma continues to flow along the strip to the upper wick where it will wash away the water soluble dye marking from the control window to provide a visual confirmation that the sample addition step of the testing procedure has been completed. In the event that the device which is employed does not include the optional control window, the user may merely allow a predetermined period of time, for example 5 minutes, to pass to ensure that the sample addition step of the testing procedure has been completed.

A buffer liquid, preferably saline, is then added to the buffer well via the buffer port. The buffer liquid is absorbed from the well by an upstream portion of the lower wick(s) extending into the well, and as the buffer liquid flows laterally along the length of the lower wick, it mobilizes the dried labeled reagent and carries the mobilized labeled reagent along the length of the main strip and to the upper wick. As the labeled reagent passes through the detection zone on the main strip, it binds with any IgE antibody analyte bound to the immobilized IgE allergen particles, thus resulting in a visibly detectable marking. The indicia on the housing top allow correlation of any visibly detectable marking in the result windows with antibody/allergen information to determine the identities of IgE antibodies bound in the detection zone(s).

As the buffer liquid carries excess labeled reagent to the upper wick(s) and control zone(s), the labeled reagent binds with IgE antibody immobilized in the control zone to produce an additional visibly detectable marking. The appearance of the marking in each control zone provides a visual confirmation that labeled reagent has successfully passed through the detection zone and testing is completed.

Thus, the assay devices of the invention are adapted for conducting a two step assay. To facilitate use of a device according to the invention, the device may be provided in a kit in combination with a capillary device of a size effective for providing an appropriate quantity of sample for use in the device, as described above. The kit may optionally further comprise a quantity of buffer liquid, i.e., saline, which is effective for mobilizing the labeled reagent and transporting the labeled reagent along the lateral flow matrix to the control zones. In a further embodiment, a kit according to the invention may comprise a plurality of assay devices as described, a corresponding plurality of capillaries for collecting samples for application to the devices, and a supply of saline sufficient for proper use of the devices. The saline may be supplied in a single package or may be supplied in a plurality of individual packages corresponding with the plurality of assay devices.

Although the assay methods and devices according to the invention involve two steps, namely sample application followed by buffer liquid application, the methods and devices may be easily and conveniently employed without error and with confirmation that the methods have been correctly performed. That is, since a single sample port can deliver a sample to one, two or more lateral flow paths, each having a plurality of binding members, i.e., IgE antibodies of different specificities, immobilized in a detection zone, only a single sample application is required to test for a plurality of analytes, for example a plurality of IgE antibodies. Moreover, since the buffer well distributes buffer liquid to all lateral flow paths, only a single buffer liquid application is required, even when testing for a plurality of analytes such as a plurality of IgE antibodies. Further, as the control zone may be initially provided with a water soluble dye marking, without interfering with the detection reactions, a readily detectable signal, i.e., disappearance of the water soluble dye marking, indicates when the sample has successfully traversed the detection zone to the control zone and the buffer liquid may then be properly applied. Finally, a readily detectable signal occurs when the labeled reagent has successfully traversed the detection zone to the control zone by reaction of the labeled reagent with the immobilized IgE antibody in the control zone, thereby clearly signaling when the assay method is complete. Accordingly, the two step methods and devices are convenient and reliable.

Moreover, because the assay methods are conducted in two steps, and the analyte-containing sample is contacted with the immobilized specific binding pair member before it is contacted with the labeled reagent, a more accurate analyte detection method is achieved, particularly for samples which contain a plurality of non-specific binding pair members, such as a whole blood sample when IgE antibody detection is desired. The IgE antibodies are allowed to react with respective antigens in the detection zone, and, once these reactions have occurred, the labeled reagent is then transported to the detection zones by the subsequent application of buffer liquid. Surprisingly, when the labeled reagent does not interfere with the antibody-antigen reactions in the detection zones, the assay methods and devices exhibit improved sensitivity and more accurate identification of IgE antibodies is obtained.

The advantages of the methods and devices of the present invention are demonstrated in the following example.

EXAMPLE

Various assays were conducted to detect IgE antibodies in serum sample mixtures. The sample mixtures contained many different IgE antibodies, with known amounts of four IgE antibodies (e1, t3, and d1), as set forth in the following Table. The total IgE antibody content of each sample was measured and is also set forth in the Table below. For each sample mixture, a two step assay method according to the invention was conducted wherein the sample was contacted with immobilized IgE antigens in a detection zone of a lateral flow assay, after which a labeled anti-IgE antibody (on gold sol particles) was transported to the detection zone. The resulting visible color changes in the detection zone were evaluated on a scale of 0 (no color change) to 5 (indicating greatest color change), the results of which are set forth in the Table. For comparison purposes, the samples were also subjected to analysis using a one step method as commonly employed in the art, wherein the samples were contacted with the labeled anti-IgE antibody (on gold sol particles) prior to arrival of the sample in the detection zone, along the lines of the methods taught by the prior art discussed in the Background of the Invention. The resulting visible color changes in the detection zone were evaluated on the aforementioned scale, and the results are also set forth in the Table below.

| | Comparison of Two Step and One Step Assays (Concentrations in kU/1) | | | | | | | | | |
|---|---|---|---|---|---|---|---|---|---|---|
| Run | Total IgE in sample | e1 in sample | 2 step e1 score | 1 step e1 score | t3 in sample | 2 step t3 score | 1 step t3 score | d1 in sample | 2 step d1 score | 1 step d1 score |
| 1 | 1958 | 31.7 | 4 | 2 | 3.1 | 1 | 0 | 1.49 | 0 | 0 |
| 2 | 4637 | 65.8 | 4 | 3 | 28.9 | 2 | 0 | >100 | 5 | 2 |

-continued

Comparison of Two Step and One Step Assays (Concentrations in kU/1)

| Run | Total IgE in sample | e1 in sample | 2 step e1 score | 1 step e1 score | t3 in sample | 2 step t3 score | 1 step t3 score | d1 in sample | 2 step d1 score | 1 step d1 score |
|---|---|---|---|---|---|---|---|---|---|---|
| 3 | 5000 | >100 | 5 | 4 | 12.9 | 3 | 0 | >100 | 4 | 1 |
| 4 | 4064 | 55.7 | 4 | 3 | >100 | 3 | 1 | >100 | 5 | 3 |
| 5 | 523 | 0.97 | 0 | 0 | 22.2 | 3 | 2 | 2.06 | 0 | 0 |
| 6 | 114 | 4.01 | 2 | 2 | 3.29 | 1 | 0 | 2.6 | 0 | 0 |
| 7 | 384 | 38.9 | 4 | 4 | 2.29 | 1 | 0 | < | 0 | 0 |

< indicates concentration below 0.35 kU/1.

The results set forth in the Table surprisingly demonstrate that the two step method according to the invention exhibits improved sensitivity with respect to IgE antibody detection, particularly at higher antibody concentrations, as compared with the one step methods commonly taught in the prior art. Thus, the present methods and devices not only provide a convenient, point of care technique for IgE antibody testing, but also provide improved sensitivity in detection of specific IgE antibodies for improved diagnosis of allergy.

The specific illustrations and embodiments described herein are exemplary only in nature and are not intended to be limiting of the invention defined by the claims. Further embodiments and examples will be apparent to one of ordinary skill in the art in view of this specification and are within the scope of the claimed invention.

What is claimed is:

1. A two step lateral flow assay method for identifying specific IgE antibodies in a sample, comprising
    applying a blood sample to a sample port of a device, the device comprising
    a housing provided with a sample port, a buffer port upstream of the sample port, a result window downstream of the sample port, and a control window downstream of the result window,
    a buffer well upstream of the sample port and adapted to receive a quantity of liquid buffer applied through the buffer port,
    a lateral flow path within the housing, extending from the buffer well to the control window and comprising a lateral flow matrix,
    dried, labeled reagent adapted to bind IgE antibody, the labeled reagent being arranged on the lateral flow matrix downstream of the buffer well and upstream of the sample port, wherein the labeled reagent is adapted to be mobilized in the lateral flow matrix by liquid buffer passing from the buffer well along the lateral flow matrix, a plurality of IgE antigen species immobilized at respective positions on the lateral flow matrix at a first location visible through the result window, and
    a water-soluble mark located on the lateral flow matrix and visible through the control window prior to any addition of liquid to the device, wherein the water-soluble mark is dissolvable by a liquid sample that has passed through the immobilized IgE antigen species to provide a visual signal for addition of liquid buffer,
    allowing the sample to travel along the lateral flow matrix through the immobilized plurality of IgE antigen species, allowing any specific IgE antibodies in the sample to bind respective immobilized IgE antigen species, and allowing the sample to dissolve the water-soluble mark as the sample flows therethrough,
    applying a liquid buffer to the buffer port after the water-soluble mark is dissolved, allowing the liquid buffer to mobilize the labeled reagent, and allowing the immobilized liquid reagent to travel along the lateral flow matrix and bind with any IgE antibody bound to the immobilized IgE antigen species, and
    detecting any labeled reagent in the result window and relating the detected labeled reagent to a specific IgE antibody in the sample.

2. The two step method according to claim 1, wherein the sample is a whole blood sample, and the device is adapted to filter the sample and deliver a filtered sample substantially free of red blood cells to the lateral flow matrix.

3. The two step method according to claim 2, wherein the sample is filtered by passing the sample through at least one layer of material adapted to aggregate red blood cells therein.

4. The two step method according to claim 3, wherein the at least one layer of material includes an agglomerating agent.

5. The two step method according to claim 1, wherein travel of the labeled reagent to a second location visible through the control window is detected by a visible change at the second location.

6. The two step method according to claim 1, wherein the labeled reagent comprises anti-IgE antibody.

7. The two step method according to claim 1, wherein the sample is whole blood.

8. The two step method according to claim 1, wherein the lateral flow matrix comprises, at its upstream end, an upstream wick which is adapted for delivery of a liquid buffer from the buffer well to the lateral flow matrix.

9. The two step method according to claim 8, wherein the labeled reagent is provided on the upstream wick of the lateral flow matrix.

10. The two step method according to claim 9, wherein the lateral flow matrix comprises, at its downstream end, a downstream wick on which unlabeled IgE or anti mouse antibody is immobilized at a location separate and downstream from the first location and visible through the control window.

11. The two step method according to claim 10, wherein the water-soluble mark is located on the downstream wick.

12. The two step method according to claim 9, wherein the lateral flow matrix comprises a lateral flow strip comprising a nitrocellulose matrix or a polymer matrix between the upstream wick and the downstream wick.

13. The two step method according to claim 12, wherein the strip comprises a nitrocellulose matrix.

14. The two step method according to claim 1, wherein the device comprises two lateral flow paths and the housing is provided with one sample port, one buffer port, two result windows and two control windows, and wherein each lateral flow path is associated with a respective result window and a respective control window.

15. The two step method according to claim 14, wherein the two lateral flow paths are substantially parallel.

16. The two step method according to claim 1, wherein the device comprises a blood separation system between the sample port and the lateral flow matrix.

17. The two step method according to claim 16, wherein the blood separation system comprises at least one layer of material adapted to aggregate red blood cells therein.

18. The two step method according to claim 17, wherein the blood separation system comprises at least one layer of glass fiber filter paper including agglomerating agent.

19. The two step method according to claim 18, wherein the agglomerating agent comprises mannitol.

20. The two step method according to claim 16, wherein the blood separation system includes a lower layer which extends from a position below the sample port to the lateral flow matrix and is adapted to provide fluid communication between the blood separation system and the lateral flow matrix.

21. The two step method according to claim 1, wherein the plurality of IgE antigen species are attached to immobilized particles which exhibit hydrophilic groups on their surface and have a diameter smaller than a smallest inner dimension of flow channels of the lateral flow matrix at the first location, the particles being immobilized on the lateral flow matrix at the first location.

22. The two step method according to claim 1, wherein the housing includes indicia adjacent the result window distinguishing the locations of the respective species of IgE antigen.

23. The two step method according to claim 1, wherein the labeled reagent comprises anti-IgE antibody labeled with a metal sol.

24. The two step method according to claim 23, wherein the metal sol comprises a gold sol.

25. The two step method according to claim 1, wherein the device is provided in a kit for identifying specific IgE antibodies in a sample, and wherein the kit comprises a capillary for collecting a quantity of whole blood, and the device is adapted to receive the quantity of whole blood from the capillary.

26. The two step method according to claim 25, wherein the kit further comprises liquid buffer in an amount sufficient to mobilize the labeled reagent and transport the labeled reagent along the lateral flow matrix to the control window.

27. The two step method according to claim 1, wherein unlabeled IgE or anti mouse antibody is immobilized on the lateral flow matrix at a location separate and downstream from the first location and visible through the control window.

28. The two step method according to claim 1, wherein unlabeled reagent capable of binding with the labeled reagent is immobilized on the lateral flow matrix at a location separate and downstream from the first location and visible through the control window.

29. The two step method according to claim 1, wherein the lateral flow matrix includes a lateral flow strip extending from upstream of the sample port through the first location and operable to receive sample applied to the sample port.

30. The two step method according to claim 1, wherein the device comprises at least two lateral flow paths within the housing, each extending from the buffer well to a downstream location and comprising a lateral flow matrix, wherein dried, labeled reagent adapted to bind IgE antibody is arranged on each lateral flow matrix downstream of the buffer well and upstream of the sample port, wherein the labeled reagent is adapted to be mobilized in the respective lateral flow matrix by liquid buffer passing from the buffer well along the lateral flow matrix, wherein a plurality of IgE antigen species is immobilized at respective positions on each lateral flow matrix at a first location visible through the result window, and wherein a water-soluble mark is located on each lateral flow matrix and visible through the control window prior to any addition of liquid to the device and each water-soluble mark is dissolvable by a liquid sample that has passed through the respective immobilized IgE antigen species to provide a visual signal for addition of liquid buffer, the method comprising:

applying a blood sample to the sample port, allowing the sample to travel along each lateral flow matrix through the respective immobilized plurality of IgE antigen species, allowing any specific IgE antibodies in the sample to bind respective immobilized IgE antigen species, and allowing the sample to dissolve the respective water-soluble marks as the sample flows there through, applying a liquid buffer to the buffer port after the water-soluble marks are dissolved, allowing the liquid buffer to mobilize the labeled reagent, and allowing the immobilized liquid reagent to travel along the respective lateral flow matrix and bind with any IgE antibody bound to the respective immobilized IgE antigen species, and detecting any labeled reagent in the result window and relating the detected labeled reagent to a specific IgE antibody in the sample.

31. The two step method according to claim 30, wherein the device further comprises unlabeled IgE antibody immobilized on each lateral flow matrix at a second location separate and downstream from the first location and visible through the control window.

32. The two step method according to claim 31, wherein each lateral flow matrix comprises, at its downstream end, a downstream wick on which unlabeled IgE or anti mouse antibody is immobilized.

33. The two step method according to claim 32, wherein each water-soluble mark is located on the respective downstream wick.

34. The two step method according to claim 32, wherein each lateral flow matrix comprises a nitrocellulose matrix between the upstream wick and the downstream wick and wherein the first location at which the plurality of IgE antigen species are immobilized is on the nitrocellulose matrix.

35. The two step method according to claim 34, wherein each nitrocellulose matrix extends upstream of the sample port.

36. The two step method according to claim 30, wherein each lateral flow matrix comprises, at its upstream end, an upstream wick which is adapted for delivery of a liquid buffer from the buffer well to the lateral flow matrix.

37. The two step method according to claim 36, wherein the labeled reagent is provided on the upstream wick of each lateral flow matrix.

38. The two step method according to claim 30, wherein the device comprises two lateral flow paths and the housing is provided with one sample port, one buffer port, two result windows and two control windows, and wherein each lateral flow path is associated with a respective result window and a respective control window.

39. The two step method according to claim 30, further comprising a blood separation system between the sample port and the lateral flow matrices.

40. The two step method according to claim 39, wherein the blood separation system includes a lower layer which extends from a position below the sample port to each lateral flow matrix and is adapted to provide fluid communication between the blood separation system and each lateral flow matrix.

41. The two step method according to claim 30, wherein the plurality of IgE antigen species are attached to immobilized particles which exhibit hydrophilic groups on their surface and have a diameter smaller than a smallest inner dimension of flow channels of the lateral flow matrices at the first location, the particles being immobilized on the lateral flow matrices at the first location.

42. The two step method according to claim 30, wherein the housing includes indicia adjacent the result window distinguishing the locations of the respective species of IgE antigen.

43. The two step method according to claim 30, wherein the labeled reagent comprises anti-IgE antibody labeled with a metal sol.

44. The two step method according to claim 43, wherein the metal sol comprises a gold sol.

45. The two step method according to claim 30, wherein the device is provided in a kit for identifying specific IgE antibodies in a sample, and wherein the kit comprises a capillary for collecting a quantity of whole blood, and the device is adapted to receive the quantity of whole blood from the capillary.

46. The two step method according to claim 45, wherein the kit further comprises liquid buffer in an amount sufficient to mobilize the labeled reagent and transport the labeled reagent along the lateral flow matrices to the control window.

* * * * *